(12) United States Patent
Mertens et al.

(10) Patent No.: US 8,956,813 B2
(45) Date of Patent: Feb. 17, 2015

(54) METHOD AND SYSTEM FOR DETECTION OF A SELECTED TYPE OF MOLECULES IN A SAMPLE

(75) Inventors: Johann Mertens, Tres Cantos Madrid (ES); Francisco Javier Tamayo De Miguel, Tres Cantos Madrid (ES); Montserrat Calleja Gomez, Tres Cantos Madrid (ES); Daniel Vega Ramos, Tres Cantos Madrid (ES); Celia Rogero Blanco, Torrejon de Ardoz Madrid (ES); Jose Angel Martin Gago, Cantoblanco Madrid (ES); Carlos Briones Llorente, Torrejon de Ardoz Madrid (ES)

(73) Assignees: Consejo Superior de Investigaciones Cientificas, Madrid (ES); Instituto Nacional de Tecnica Aeroespacial, Torrejon de Ardoz (ES)

( * ) Notice: Subject to any disclaimer, the term of this patent is extended or adjusted under 35 U.S.C. 154(b) by 711 days.

(21) Appl. No.: 12/739,193
(22) PCT Filed: Sep. 23, 2008
(86) PCT No.: PCT/EP2008/062709
§ 371 (c)(1), (2), (4) Date: Aug. 23, 2010
(87) PCT Pub. No.: WO2009/053195
PCT Pub. Date: Apr. 30, 2009

(65) Prior Publication Data
US 2011/0039255 A1 Feb. 17, 2011

(30) Foreign Application Priority Data
Oct. 22, 2007 (EP) .................................... 07380283

(51) Int. Cl.
*C12Q 1/68* (2006.01)
*C12M 1/34* (2006.01)
(Continued)

(52) U.S. Cl.
CPC ........... *G01N 33/54373* (2013.01); *B82Y 35/00* (2013.01)
USPC ....... 435/6.1; 435/6.11; 435/287.2; 536/23.1; 536/24.3; 73/504.15; 73/862.634; 73/862.639

(58) Field of Classification Search
USPC ............. 435/6.1, 6.11, 287.2; 536/23.1, 24.3; 73/504.15, 862.634, 862.639
See application file for complete search history.

(56) References Cited

U.S. PATENT DOCUMENTS

| 5,807,758 | A | * | 9/1998 | Lee et al. ....................... 436/526 |
| 6,763,705 | B1 | * | 7/2004 | Thundat et al. .............. 73/64.53 |

(Continued)

FOREIGN PATENT DOCUMENTS

| EP | 1 226 437 | 7/2002 |
| EP | 1 575 058 | 9/2005 |

(Continued)

OTHER PUBLICATIONS

Agilent Impedance Ananlyzer brochure, printed on Apr. 2007, pp. 1-5.*

(Continued)

*Primary Examiner* — Narayan Bhat
(74) *Attorney, Agent, or Firm* — Ostrolenk Faber LLP

(57) ABSTRACT

The present invention refers to a method for detecting molecules and/or substances within a sample based on the use of a microcantilever system. The method comprises the variation of a certain condition such as humidity so as the mechanical feature analyzed varies with a characteristic pattern while the target molecule is bound to the detector. The invention also refers to the system used to carry out such method.

18 Claims, 7 Drawing Sheets

(51) Int. Cl.
| | |
|---|---|
| *C07H 21/02* | (2006.01) |
| *C07H 21/04* | (2006.01) |
| *G01C 19/00* | (2013.01) |
| *G01L 1/04* | (2006.01) |
| *G01N 33/543* | (2006.01) |
| *B82Y 35/00* | (2011.01) |

(56) References Cited

U.S. PATENT DOCUMENTS

| | | | | |
|---|---|---|---|---|
| 7,148,017 | B1* | 12/2006 | Craighead et al. | 435/7.1 |
| 7,282,329 | B2* | 10/2007 | Manalis et al. | 435/6.11 |
| 2004/0197806 | A1* | 10/2004 | Yoshida et al. | 435/6 |
| 2004/0208788 | A1* | 10/2004 | Colton | 422/68.1 |
| 2006/0019299 | A1* | 1/2006 | Kang et al. | 435/6 |
| 2006/0155478 | A1* | 7/2006 | Roukes et al. | 702/19 |
| 2007/0128623 | A1* | 6/2007 | Park et al. | 435/6 |

FOREIGN PATENT DOCUMENTS

| | | |
|---|---|---|
| EP | 1 733 399 | 12/2006 |
| WO | WO 02/20832 | 3/2002 |
| WO | WO 03/091458 | 11/2003 |
| WO | WO 2007/006834 | 1/2007 |

OTHER PUBLICATIONS

International Search Report dated Feb. 3, 2009.

H.G. Craighead, "Nanoelectromechanical Systems", *Science*, 290:1532-1535 (2000).

M. Li et al., "Ultra-sensitive, NEMS-based cantilevers for sensing, scanned probe and very high-frequency applications", *nature nanotechnology*, 2:114-120 (2007).

B. Ilic et al., "Mechanical resonant immunospecific biological detector", *Applied Physics Letters*, 77(3):450-452 (2000).

A. Engel et al., "Atomic force microscopy: a powerful tool to observe biomolecules at work", *trends in Cell Biology*, 9:77-80 (1999).

P. Vettiger et al., "The "Millipede"—More than one thousand tips for future AFM data storage", *IBM J. Res. Develop.*, 44(3):323-340 (2000).

G. Meyer et al., "Simultaneous measurement of lateral and normal forces with an optical-beam-deflection atomic force microscope", *Appl. Phys. Lett.*, 57(20):2089-2091 (1990).

R. McKendry et al., "Multiple label-free biodetection and quantitive DNA-binding assays on a nanomechanical cantilever array", *PNAS*, 99(15):9783-9788 (2002).

S. Jeon et al. "Instant curvature measurement for microcantilever sensors", *Applied Physics Letters*, 85(6):10831084 (2004).

C. Briones et al., "Nucleic Acids and Their Analogs as Nanomaterials for Biosensor Development", *Current Nanoscience*, 2:257-273 (2006).

S. Biswal et al., "Nanomechanical Detection of DNA Melting on Microcantilever Surfaces", *Anal. Chem.*, 78:7104-7109 (2006).

J. Mertens, "Label-free detection of DNA hybridization based on hydration-induced tension in nucleic acid films", *nature nanontechnology*, 3:301-307 (2008).

J. Stachowiak, "Chemomechanics of Surface Stresses Induced by DNA Hybridization", *Langmuir*, 22:263-268 (2006).

Q. Zhu et al., "Real-time, label-free, all-electrical detection of *Salmonella typhimurium* using lead titanate zirconate/gold-coated glass cantilevers at any relative humidity", *Sensors and Actuators B*, 125:379-388 (2007).

* cited by examiner

METHOD AND SYSTEM FOR DETECTION OF A SELECTED TYPE OF MOLECULES IN A SAMPLE

FIELD OF THE INVENTION

The invention is related to the field of chemical and/or biological analysis and detection using micro- or nano-mechanical structures, such as micro- or nano-cantilevers, micro- or nano-bridges, micro- or nano-membranes, etc.

STATE OF THE ART

There is an increasing interest in systems and methods based on micromechanical and nanomechanical elements [H. G. Craighead, "*Nanoelectromechanical systems*", Science 290, pp. 1532-1535 (2000) and M. Li, H. X. Tang, M. L. Roukes, "*Ultra-sensitive NEMS-based cantilevers for sensing, scanned probe and very high-frequency applications*", Nature Nanotechnology 2, pp. 114-120 (2007)] Micro- and nanomechanical systems (MMS) and microcantilever-based devices are two relevant examples of this kind of systems.

For example, microcantilevers can be used for ultrasensitive nanomechanical biological and chemical sensors [B. Ilic, D. Czaplewski, H. G. Craighead, P. Neuzil, C. Campagnolo and C. Batt, "*Mechanical resonant immunospecific biological detector*", Applied Physics Letters 77, pp. 450-452 (2000)]. Real time measurement of the shape, profile, motion, stress and/or strain is very valuable for monitoring the mechanical response of, for example, chemical and biological sensors that are based on the shape, profile, motion, stress or strain of MMS or micro- or nano-cantilevers.

MMS and microcantilever systems include systems based on cantilevers having a fixed end and a movable end; in these systems, it is usually the displacement and/or movement of the "free" end what is detected. However, there are also systems based on cantilevers clamped at both ends, in which the movement of the central part can be detected. Further, there are other micro- and nanomechanical structures that are movable and flexible, such as doubly clamped paddles whose "easy" direction of motion corresponds to the torsion of the paddle around the axis of the hinges that connect the paddle to a frame (basically, like a square racket fastened to a frame by two opposite handles of the racket, extending along an axis). Other known systems use membranes that are connected to a frame through two sets of hinges, which allows two angular degrees of freedom.

In chemical/biological sensors based on MMS and microcantilevers, the surface of the micro- or nanomechanical element is sensitised with receptor or "probe" molecules that selectively recognize the targeted substance. The interaction between the immobilized probe and the targeted substance on the surface of the micro- or nanomechanical element produces a change of the shape, profile, strain, stress and motion (vibration) of the mechanical element. This change is usually monitored by measuring the displacement of a representative part of the mechanical element (usually the free end of a singly clamped microcantilever, although it can also be the centre of a doubly clamped microcantilever, a part of a membrane sheet, etc.). This displacement can be in the order of about 1-100 nanometers (nm) and in many cases it is necessary to obtain a resolution better than 1 nm, depending on the application. For the readout of the displacement, there are several techniques such as capacitive detection, detection based on tunnel current, optical interferometry, piezoresistive readout and the optical beam deflection technique.

Examples of MMS and microcantilever systems are disclosed in, for example:

Engel et al, "*Atomic force microscopy: a powerful tool to observe biomolecules at work*", Trends in Cell Biology, Volume 9, pp. 77-80 (1999)

P. Vettiger et al, "*The millipede-more than one thousand tips for future AFM storage*", IBM J. Res. Develop., Volume 44, Number 3, pp. 323-339 (2000).

WO-A-2001/33226
WO-A-2003/091458
WO-A-2005/086172
WO-A-2007/006834

The optical beam deflection method is maybe the most sensitive one, and it has the advantage that it can be easily implemented. FIG. 1 schematically illustrates a conventional prior art arrangement for optical beam deflection. A light source (such as a laser source) produces a light beam (such as a laser light beam, in the visible, ultraviolet or infrared spectrum) that is focused (that is, either directly focused or via focusing means involving, for example, one or more mirrors, etc.) onto the part of the mechanical element where the displacement is to be measured, for example, onto the end of a microcantilever forming part of a micromechanical device. The deflection of the beam reflected off the cantilever is measured with a position sensitive detector (such as a photodetector, for example, a segmented photodetector, a continuous position sensing photodetector, a photodetector array, a CCD, etc.). For example, a segmented photodetector can be employed that is split into two segments. The deflection of the cantilever produces a displacement of the reflected laser spot on the photodetector. Thus, the difference in photocurrents between the two segments is proportional to the cantilever deflection. Similarly, the optical beam deflection technique can be applied to other types of mechanical elements such as doubly clamped cantilevers, membrane sheets, micropaddles, etc. Similarly, it can be applied for readout of other types of displacements instead of the out-of-plane displacement, such as the torsional motion of microcantilevers and micropaddles, etc. (G. Meyer and N. M. Amer, "*Simultaneous measurement of lateral and normal forces with an optical-beam-deflection atomic force microscope*", Applied Physics Letters, vol. 57, pp. 2089-2091 (1990)).

This system is suitable for measuring both the static and the dynamic behaviour of mechanical elements such as cantilevers, for example, the maximum deflection, mean value of deflection, amplitude at a reference frequency (the element can be externally driven by an excitation force oscillating at the reference frequency), phase of the motion with respect to a external driving signal, frequency, etc. The measured static displacement, amplitude, frequency, etc., can then be related to an object that is to be measured and that interacts with the cantilever, and with signals and/or procedures used to stimulate the object and/or the cantilever.

Now, the technique described above is practical when the displacement/movement of a single part of a single mechanical element is to be measured. However, this technique cannot be applied to devices based on arrays comprising a plurality of mechanical elements, in which the displacement/movement of each element needs to be measured. These devices provide for multifunctionality and for higher speed and/or more complete information than devices based on a single mechanical element. For instance, chemical and biological sensors based on microcantilever arrays can detect several substances by sensitising each cantilever with a different receptor [R. McKendry R et al., "Multiple label-free biodetection and quantitative DNA-binding assays on a nanomechanical cantilever array", Proceedings of the National Academy Of Sciences of the United States Of America 99, pp. 9783-9788, (2002)]. In addition, it may be advantageous to obtain information about the displacement of several regions of the mechanical element, so as to obtain more information about the external stimulus that is measured or about different stimuli that interact with different parts of the mechanical element.

The patent application WO-A-2005/086172 mentioned above discloses a system such as the one illustrated in FIG. 2, wherein the microcantilevers of an array are illuminated by a single laser light source placed on a one-dimensional voice-coil actuator whereby the incident laser beam is made to periodically scan the array in a direction perpendicular to the longitudinal axes of the microcantilevers. Thus, the free end of each microcantilever of the microarray is sequentially illuminated. When the laser beam reflects off the surface of a microcantilever of the array, an increase of the total photocurrent of a position sensitive detector (that is arranged to collect the laser beam reflected off the cantilever) is detected, this increase corresponding to the peaks of the detected photocurrent. When the increase of photocurrent is detected, the position coordinates of the corresponding spot where the reflected laser beam hits the photodetector are determined on the basis of the photocurrent signals generated by the detector, and these coordinates can then be used to determine the deflection of the cantilever.

On the other hand, it is sometimes necessary to measure not only the displacement of a specific part of the cantilever or other type of mechanical element, but rather the general change in curvature or general shape of the cantilever or similar element, or of a part thereof. Thus, a technique is known which has been applied to microcantilever sensors that utilizes the bending of a cantilever having a bilayer structure (e.g., a thin gold film on silicon or silicon nitride). The curvatures of the cantilevers undergo a change in response to any change of temperature or differential surface stress due to molecular adsorption. To obtain the change of curvature radius, a measurement system is known based on the use of eight light emitting diodes focused on various positions of a gold-coated silicon cantilever. The deflection at each point on the cantilever is measured with subnanometer precision by a position sensitive detector using the optical beam deflection technique, and thus the curvature of the cantilever is obtained. This method is disclosed in Sangmin Jeon, et al., *"Instant curvature measurement for microcantilever sensors"*, *Applied Physics Letters*, vol. 85, no. 6, pp. 1083-1084 (2004).

In addition to cantilever systems in which the displacement of a specific part of the cantilever is to be measured, or in which the curvature of the cantilever is to be measured, there may be mechanical structures such as membrane sheets sensitised in different regions to different stimulus, in such a way that to obtain the information over each stimulus is necessary to measure the displacement of each sensitised region of the mechanical structure.

WO-A-2007/006834 mentioned above discloses a system as the one illustrated in FIG. 3. The system is arranged to detect relative displacement and/or vibration characteristics of a plurality of points placed in a plurality of elements forming part of a mechanical structure, and comprises a light source arranged to generate at least one light beam, a position sensitive detector arranged to receive the light beam when reflected off the mechanical structure and to produce at least one output signal in response to receipt of said light beam, an electronic control system, and scan means for relative displacement of said light beam with respect to the mechanical structure so as to scan said mechanical structure with the light beam, following instructions from the electronic control system. The electronic control system is arranged to control the scan means so as to displace the light beam along the mechanical structure along a first trajectory (A), so as to detect a plurality of subsequent reference positions (C) along said first trajectory (A), wherein said electronic control system is operatively associated with said position sensitive detector so as to determine said reference positions C as a result of an analysis of at least one output signal from said position sensitive detector. Further, the electronic control system is arranged to control the scan means so as to displace the light beam along the mechanical structure along a plurality of second trajectories (B), each of said second trajectories (B) being associated with one of said reference positions (C). The electronic control system is further arranged to obtain, during displacement of the light beam along each of said second trajectories (B), a plurality of position signal outputs from said position sensitive detector.

With this system, it is possible to obtain real-time measurements of the displacement and motion of a plurality of selected locations of a mechanical structure or of a region of interest of that structure. This provides more information on how the mechanical structure changes in relation to the object to be measured, which would in turn imply higher sensitivity and higher signal-to-noise ratio. For instance, in some microcantilever sensors, the curvature along the microcantilever is related to molecules adsorbed on the surface of the microcantilever. To obtain its curvature, it is necessary to measure the displacement of several locations along the microcantilever.

In the case of chemical sensors or biosensors, the mechanical element (such as a nano- or micro-cantilever) used for detection has, as mentioned above, a portion arranged to interact with the type (or types) of molecules to be detected, so that the presence of said molecules in a sample in contact with said portion causes a change in its mechanical properties, such as a change in curvature, surface stress and/or vibration characteristics, which can be detected with, for example, the methods described above.

For example, one of the major surfaces of the cantilever can be functionalized with a layer of substances or molecules acting as receptors or "probes". The functionalization can be performed via chemical or physical interactions of that substances or molecules with the surface of the cantilever. For instance, a cross-linking molecule can be used, in which one of their ends form covalent bonds with the cantilever surface and the other end has strong affinity to the probe molecule. Most widely used methods are based on silanization of the cantilever surface, as well as on the immobilization of self-assembled monolayers of probe molecules on the cantilever surface. The receptors or probes can be chosen to study their interaction with other target substance or molecule, and eventually to determine the concentration of the targeted substance in the sample analyzed. In this application, receptors specifically bind the target, and this specific interaction is often referred to as molecular recognition. Examples of receptor or probe molecules include nucleic acids (DNA, RNA, PNA or others), proteins (antibodies, enzymes, or others), alternative biopolymers, etc. The target molecule or substance can be found diluted in a gaseous sample or in a liquid sample. Biological targets are often found in aqueous solutions [Briones, C. and Martin-Gago, J. A., *"Nucleic acids and their analogs as nanomaterials for biosensor development"*, *Current Nanoscience* 2, 257-273 (2006)].

For example, a mechanical element can have at least one receptor surface (for instance a cantilever in which one of the sides has been functionalized with molecular receptors such as DNA, antibodies etc.) arranged (for instance, the cantilever immersed in a buffer solution in a microfluidic cell with inlet and outlet channels to inject the buffer solution containing the target molecules) to interact with at least one kind of molecules when present in a sample in contact with said receptor surface. The mechanical element can be arranged so that at least one detectable mechanical feature (such as the curvature of a portion of the element, the position of a surface portion of the element, and/or a vibration characteristic) of said element changes when said receptor surface interacts with said target molecules, and subsequently a measurement process is carried out to determine if said mechanical feature has changed and the extent of such a change. If it has changed (to a certain extent), it is assumed that the sample contains the kind of molecules that can specifically interact with the immobilized probe molecules. Sometimes, the change in the mechanical feature is monitored over time, that is, the element is brought in contact with the sample and the mechanical feature (such as the curvature of a cantilever) is measured, and it is detected if it changes in time. If such a change is detected, it is assumed that the target molecules were present in the sample.

Nevertheless, the techniques so far developed imply some problems:

Sometimes, the detected "change" arises from other factors and not from the interaction between the receptor surface and the target molecules. For example, this can be produced by non specific interactions of the target with the mechanical element, small variations in the temperature, small fluctuations in the ions in liquid solutions, fluid turbulences, index refraction changes, slow variations with the time in the positions of the optical elements that detect the mechanical element motion etc.

Also, in order to detect the change, it is necessary to monitor the mechanical element in real time, that is, basically, from the moment in which it enters into contact with the sample, so that the change must be detected while it takes place (as data regarding the feature both before and after the change must be available).

Also, the magnitude of the change (such as a change in curvature) can be fairly small, which obviously makes the detection a more difficult task.

DEFINITIONS

Antibody. A Y-shaped protein (immunoglobulin) on the surface of B cells that is secreted into the blood or lymph in response to an antigenic stimulus, such as a bacterium, virus, parasite, or transplanted organ, and that neutralizes the antigen by binding specifically to it. The detection of the formation of antibody-antigen pairs can be followed by several methods and it is the basis of many biosensors.

Antigen. A substance that stimulates the production or mobilization of antibodies. An antigen can be a foreign protein, toxin, bacteria, or other substance.

Aptamer. A nucleic acid molecule designed in vitro to specifically interact with a ligand molecule. The specificity of an aptamer-ligand pair can be as high as that of an antibody-antigen pair. The formation of an aptamer-ligand pair can be followed by several methods.

Biosensor. Analytical device comprising a biological recognition element (e.g. enzyme, receptor, DNA, antibody, or microorganism) in intimate contact with an electrochemical, optical, thermal, or acoustic signal transducer that together permit analyses of chemical properties or quantities. Shows potential development in some areas, including environmental monitoring.

Biochip. A high density array of single stranded DNA molecules bound to a solid surface (glass, silicon, etc. . . . ) to quickly recognize (hybridization) thousands of genes at a time, which facilitates high throughput analysis of thousands of genes simultaneously.

Cantilever. A mechanical structure, such as a beam, that is supported at one end; the deflection of the end is proportional to the load or acting external forces. Cantilevers are widely microfabricated using silicon technology to be used as sensors.

DNA. An organic acid and polymer composed of four nitrogenous bases—adenine, thymine, cytosine, and guanine linked via intervening units of phosphate and the pentose sugar deoxyribose. DNA is the genetic material of most organisms and usually exists as a double-stranded molecule in which two antiparallel strands are held together by hydrogen bonds between adeninethymine and cytosine-guanine.

Hybridization. The process of hydrogen bonding between two complementary strands of DNA or one each of DNA and RNA to form a double-stranded molecule.

Molecular recognition. The ability of biological molecules to specifically bind to another molecule that has a complementary shape. Molecular recognition drives all of biology, for instance, hormone and receptor or antibody-antigen interactions or the organization of molecules into larger biologically active entities MEMS. Microelectromechanical systems. Generally used to refer to systems on the micrometer scale that combine mechanical and electrical components and are fabricated using semiconductor fabrication techniques. MEMS respond to a stimulus or create physical forces (sensors and actuators). Miniature accelerometers are the most successful product in this field and are used to trigger air bags in cars. When such systems can be made with nanoscale dimensions they can be classified as NEMS.

Mismatch (or despairing). It occurs when in at least one position of a double stranded nucleic acid, both chains have two non-complementary nucleotides that do not hybridize.

Mutation. Also known as "single nucleotide polymorphism" (SNP), it is an alteration of the nucleotide sequence of a nucleic acid with respect to another reference sequence. This alteration can correspond to the substitution of one nucleotide by another, an insertion or a deletion of one or more nucleotides.

NEMS. See MEMS.

Oligonucleotide. A single stranded nucleic acid molecule of between 3 and 250 nt long that can hybridise with a complementary nucleic acid sequence.

Peptide nucleic acid (PNA). An artificial kind of nucleic acid molecule where the sugar-phosphate backbone has been replaced by a peptidomimetic structure. Each monomer of PNA is composed by a molecule of N-(2-aminoethyl)glycine linked, via a methylencarbonyl unit, to a nucleobase of the group formed by A, G, C and T. PNA exhibits unique physicochemical properties, being an uncharged, achiral and relatively rigid polymer of high biological and chemical stability.

Probe. It refers to oligonucleotides in length comprised by specific nucleotide sequences that permit total or partial hybridization with complementary target sequences under certain conditions. In the context of this invention, the probe oligonucleotides are immobilized to the micro- or nanomechanical structures, and under certain circumstances are capable of forming self-assembled monolayers on them.

Protein. A molecules composed of one or more polypeptide chains, ach composed of a linear chain of amino acids covalently linked by peptide bonds Resonance. A condition in which a vibrating system responds with maximum amplitude to an alternating driving force. The condition exits when the frequency of the driving force coincides with the natural undamped oscillatory frequency of the system.

Self-assembled monolayer (SAM). A two-dimensional film, one molecule thick, covalently assembled at an interface. Typical reagents will use the reaction of a thiol with gold or a trichlorosilane with SiOH groups.

Sensitization. See Surface Functionalization and Self-assembled monolayer.

Surface Functionalization. A method or technique to introduce chemical functional groups to a surface. This is used in biosensors to immobilize the biomolecular receptors on the sensor.

Strain. It refers to the geometrical expression of deformation caused by the action of stress on a physical body.

Stress. It refers to a measure of force per unit area within a body.

Surface Stress. The strain derivative of the total free surface energy divided by the surface area.

Target sequences. Molecules or sequences of nucleic acids present in the sample analyzed which are susceptible to hybridize with the oligonucleotide probes immobilized.

DESCRIPTION OF THE INVENTION

A first object of the invention is a method for detection of a selected type of molecules or substance in a sample, comprising the steps of:
a) bringing a receptor surface of a mechanical element in contact with the sample, said receptor surface being arranged to interact with said molecules or substance when said molecules or substance are present in said sample, the mechanical element being arranged so that at least one detectable mechanical feature of said element changes when said receptor surface interacts with said molecules or substance;
b) measuring said mechanical feature to obtain data regarding said mechanical feature;
c) based on said data, determining if the sample contains said type of molecules or substance;
characterized in that at least one condition to which at least the receptor surface of the mechanical element is subjected is varied, whereby said mechanical feature is measured a plurality of times, so that the data regarding said mechanical feature are obtained for different values of said condition, whereby the relation between said data and said values of the condition are used to determine if the sample contains said type of molecules or substance or to determine associative phenomena between the receptor surface and the detected molecules or substance.

Therefore, by means of the method of the invention, instead of just measuring the "absolute" value of the mechanical feature (so as to detect, for example, an "absolute" change in curvature), which can be small or be hidden by other changes in external parameters for which the mechanical element is also sensitive or by a change in the calibration of the measurement apparatus, the mechanical feature is detected under varying conditions. Thus, the way the mechanical feature changes under these conditions can be used to determine whether the relevant target molecules or substance are present in the sample.

This is possible due to the fact that the interaction between the molecules or substance to be detected and the mechanical element themselves and/or between said molecules and the probe molecules attached to the receptor surface can vary according to the conditions to which the receptor surface is subjected. Then, the binding of the molecules to the receptor change the mechanical feature vs. the condition. Examples of conditions that can be varied are the temperature, the relative humidity, the pH and ionic strength of the fluid or solvent in which the mechanical element is placed, the relative content of a mixture of gases or liquids in which the cantilever is placed (for instance, the humidity effect can be similarly obtained in a mixture of water-hydration and ethanol-dehydration) the radiation to which the receptor surface is subjected, the electrical field, the magnetic field, etc.

This method for detecting the presence of the molecules in the sample is advantageous, as it increases sensitivity (it is no longer dependent only on the absolute "magnitude" of the change induced when the molecules become coupled to the receptors) and also makes it possible to check the presence without any need for comparing the relevant mechanical feature before and after subjecting the sensor element to the sample. It is sufficient to perform the measurements after having subjected the mechanical element to contact with the sample, as what is measured is the way said mechanical feature varies when the condition is changed, and not the way it varies after the mechanical element has been brought in contact with the sample.

Thus, in the present invention, instead of measuring the variation of the mechanical feature over time, the variation of the mechanical feature is measured for different values of the condition, such as different temperatures, different levels of relative humidity, etc.

That is, the "interaction" between the molecules to be detected and the receptor surface does not any longer have to be "detected" in real time. Instead, using the method according to the invention, the mechanical element (for example, a microcantilever which can form part of a microcantilever array) can be brought in contact with the sample and, at a later stage, be analysed by means of the method of the invention. Based on previous knowledge regarding the behaviour of the relevant mechanical feature of the element (such as its curvature) when the condition (such as the relative humidity) is changed, with and without interaction between the receptor surface and the molecules to be detected, it is thus possible to determine whether said molecules are present (that is, interacting with the receptor surface, basically, coupled to it) or not. Thus, the difference in "behaviour" of the mechanical feature when the condition changes, depending on whether the molecules to be detected are present or not, implies what could be called a "fingerprint" of said molecules, thus allowing the presence thereof to be determined using the method of the invention.

In addition to the detection of a certain target molecule or substance with high sensitivity, the method allows for detection limits under 1 fM of target DNA, the method of the invention allows to determine different phenomena occurring between the detected molecule and the receptor, that is, phenomena relating to the manner in which the molecules (receptor and target) become associated or bind each other.

This can be easily explained by reference to a specific case, for instance, when the method is applied to the detection of a DNA molecule in a sample. In such a case, the receptor surface can be functionalized with probe nucleic acid (typically, DNA) molecules complementary to the molecule (the complete molecule or a specific part of its sequence) to be detected on the sample. When the 100% sequence complementarity is present between probe and target, a total hybridization will be produced on the surface of the cantilever. Thereafter, as explained above, the method implies the change of a certain condition (such as humidity) in order to obtain the "fingerprint" of the molecule under changing values of said condition (for example relative humidity). However, if there is not 100% complementarity but, for instance, the target molecule differs in a single nucleotide (or even in two or more nucleotides in different mismatching positions), the hybridization may still occur (depending on the experimental conditions) although the "fingerprint" will be different due to the different behaviour of the probe-target pair. This application is very important in the fields of molecular biology and genomics since it allows the analysis of mutations or SNPs (single nucleotide polymorphisms) present in a certain gene or genes, in a simple and efficient manner.

This particular realization of the invention can be considered the more clear and significant example, although the method is applicable to the determination of other associative phenomena between molecules including interactions such as antibody-antigen or aptamer-ligand, as well as adhesion phenomena between cells, cell-surface, virus-cell, etc.

Due to the high sensitivity achieved by the method of the invention (femtomolar sensitivity) when applied to nucleic acid detection, it may be possible to avoid previous amplification of the sample. The labelling of the sample is also avoided. Thus, the method of the present invention is of direct application in biotechnology without the need of costly, time-consuming and complicated processing of the sample.

In a preferred embodiment of the invention the condition to be varied is the relative humidity (RH). When the RH to which the receptor surface of the mechanical element is subjected is varied, then said mechanical feature is measured for different values of the RH, so that the data regarding said mechanical feature are obtained for different levels of humidity and the relation between said data and said levels of humidity is used to determine if the sample contains said type of molecules or substances and, in the case of nucleic acid molecules, its total or partial complementarity with the immobilized probes.

It has been found that the relative humidity can be an especially useful parameter in this context, as the change in relative humidity can substantially affect the interaction between many types of molecules when bound to a surface. Changes of the relative humidity tune the number of water molecules that surround the molecules. The hydration pattern of biomolecules plays a critical role in its biological function and structure. In addition, the hydration of the molecules changes the interactions between themselves, for instance: hydration forces, dipole-dipole forces, electrostatic forces, Van der Weals forces, solvation forces etc.

Thus, when the relative humidity varies, the mechanical properties of the layer of molecules attached to the receptors varies, thus inducing changes in the mechanical features of the mechanical element. For example, varying the humidity the curvature of a cantilever can be changed, due to the variation in coupling between molecules attached to the receptors arranged on the mechanical element.

In the method of the invention, the inference of the presence of a target molecule in a sample, or the presence of a certain associative phenomenon between the receptor and the detected molecules comes from the measurement of what in the context of the invention has been called mechanical feature. This term refers to a certain feature which is measured in the mechanical element of the biosensor when some change in its mechanical properties is induced by the binding of the molecule to the receptor surface. The mechanical feature to be measured may be selected from the position of a portion of the mechanical element or at least one vibration characteristic of the mechanical element or preferably the surface stress on a portion of the mechanical element.

In a preferred embodiment of the invention the step of measuring the mechanical feature comprises directing a light beam against a surface of said mechanical element, receiving a light beam reflected off said mechanical element with a position sensitive detector (2 in FIG. 8)) arranged to produce at least one output signal in response to receipt of said light beam. Nevertheless, any other means adapted for measuring the mechanical feature are of course within the scope of the present invention as a skilled person would readily realise.

Typically, the method of the invention is applicable to the detection of almost any kind of substance as each substance would have a classic "fingerprint", nevertheless the method is especially useful in the biological field, with applications in biotechnology and biomedicine. Among different molecules to be detected, DNA, RNA, proteins and peptides are specially preferred target molecules since they show a very fluctuating behaviour when an experimental condition such as relative humidity is changed. The method is also adapted to determine and analyze associating phenomena between this kind of molecules, for example, nucleic acid hybridization phenomenon or antigen-antibody binding phenomenon. In the case of DNA or RNA hybridization phenomena, mismatches in one or more nucleotides between probe and target can be analysed and identified. Thus, the method is a powerful tool for the analysis and identification of single nucleotide polymorphisms (SNPs) in an easy an efficient manner. Regarding antigen-antibody binding phenomenon, the antibody-epitope association is susceptible of being analysed.

On the other hand, the method is also applicable to the detection of more complex substances such as bacteria, viruses, eukaryotic cells protozoa etc. Also associating phenomena such as cell-cell adhesion phenomena or virus-cell or bacteria-cell adhesion may be analysed and identified.

In a preferred embodiment of the invention the mechanical element is a cantilever and said cantilever is part of a cantilever array, wherein the method is performed on said cantilever array so as to detect the presence of a plurality of different types of molecules in the sample, said different types of molecules being associated with different cantilevers of said cantilever array.

The second object of the invention is schematically represented in FIG. 8 and it represents a system for carrying out the method of the invention. It is a system for surface inspection arranged to detect relative displacement and/or vibration characteristics of a plurality of points of a plurality of elements (51) forming part of a mechanical structure (5) said system comprising:

- a light source (1) arranged to generate at least one light beam (11);
- a position sensitive detector (2) arranged to receive the light beam when reflected off the mechanical structure (5) and to produce at least one output signal in response to receipt of said light beam;
- an electronic control system (3);
- scan means (4) for relative displacement of said light beam with respect to the mechanical structure (5) so as to scan said mechanical structure with the light beam, following instructions from the electronic control system (3);
- wherein said electronic control system (3) is arranged to control the scan means (4) so as to displace the light beam along the mechanical structure along a first trajectory (label A in FIG. 8B), so as to detect a plurality of subsequent reference positions (C) along said first trajectory (A), wherein said electronic control system (3) is operatively associated with said position sensitive detector (2) so as to determine said reference positions (C) as a result of an analysis of at least one output signal from said position sensitive detector (2);

wherein said electronic control system (3) is further arranged to control the scan means (4) so as to displace the light beam along the mechanical structure along a plurality of second trajectories (B), each of said second trajectories being associated with one of said reference positions (C);

said electronic control system further being arranged to obtain, during displacement of the light beam along each of said second trajectories (B), a plurality of position signal outputs from said position sensitive detector (2) and characterised in that the mechanical structure is arranged within a chamber (6) with means for varying and controlling a condition (7).

This system is useful to carry out the method of the invention. In a preferred embodiment of the invention, the system comprises means for varying or controlling the relative humidity within the chamber, although means for controlling other conditions such as the temperature, the pH and ionic strength of the fluid in which the mechanical element is placed, the relative content of a mixture of gases or liquids in which the cantilever is placed, the radiation to which the receptor surface is subjected, electrical field, magnetic field etc., are also part of the present invention.

BRIEF DESCRIPTION OF THE DRAWINGS

To complete the description and in order to provide for a better understanding of the invention, a set of drawings is provided. Said drawings form an integral part of the description and illustrate a preferred embodiment of the invention, which should not be interpreted as restricting the scope of the invention, but just as an example of how the invention can be embodied. The drawings comprise the following figures.

DESCRIPTION OF A PREFERRED EMBODIMENT OF THE INVENTION

A DNA Biosensor

DNA microarrays are one of the most important biotechnological tools in the post-genomic era. They allow the parallel, high-throughput detection and quantification of many nucleic acid molecules, although these assays require several pre-hybridization steps of amplification and fluorescent labelling of the target sample that are costly, time consuming and imply limited sensitivity. Moreover, labelling of the target DNA may perturb its molecular recognition capabilities and, in parallel, the relative composition of detectable target molecules in the analyzed sample can be biased [Levicky, R., Horgan, A. "*Physicochemical perspectives on DNA microarray and biosensor technologies*". Trends Biochem. 23, 143 (2005)].

Alternatively, our research has shown that nucleic acid hybridization can rapidly and sensitively be measured without the need of markers or pre-amplification steps by measuring the surface stress generated by the intermolecular interactions between the nucleic acids anchored to a microcantilever surface, in a system with tunable relative humidity.

The method of the present invention shows that nucleic acid hybridization can rapidly and sensitively be measured without need of markers or pre-amplification of the target DNA by measuring the effect of the hydration on the intermolecular interactions between the probe nucleic acids anchored to a microcantilever surface before and after the hybridization with the target molecules. The proposed technique provides sub-femtomolar sensitivity in sample volumes of few microliters, what ensures a sensitivity of at least three orders of magnitude better than that of the current standard DNA microarrays used for biotechnological and biomedical applications. In addition, the nanomechanical transcript of the evolution of the intermolecular forces upon hydration of the DNA bio-layer allows discerning between perfectly matched and single-nucleotide mismatched dsDNA at room temperature.

I—Description of the Technique

Figure 1:
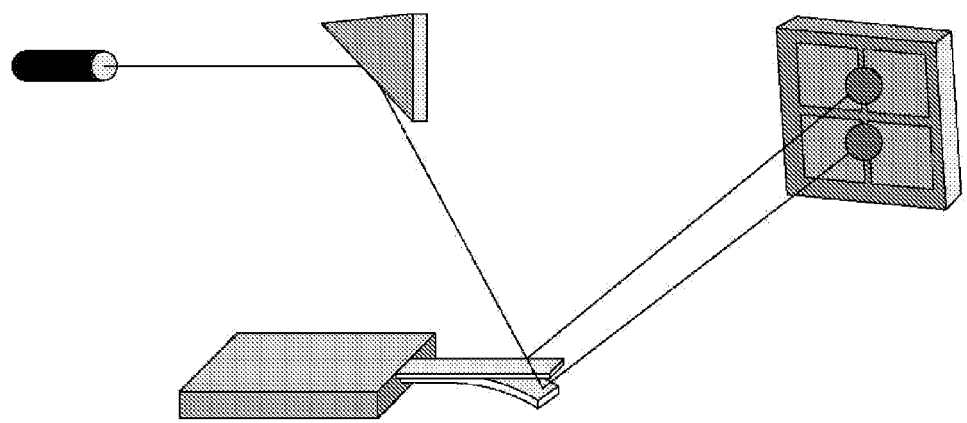
FIGS. 1, 2, 3A and 3B are schematic views of different prior art system for cantilever read-out using the optical beam deflection technique.
Figure 2:
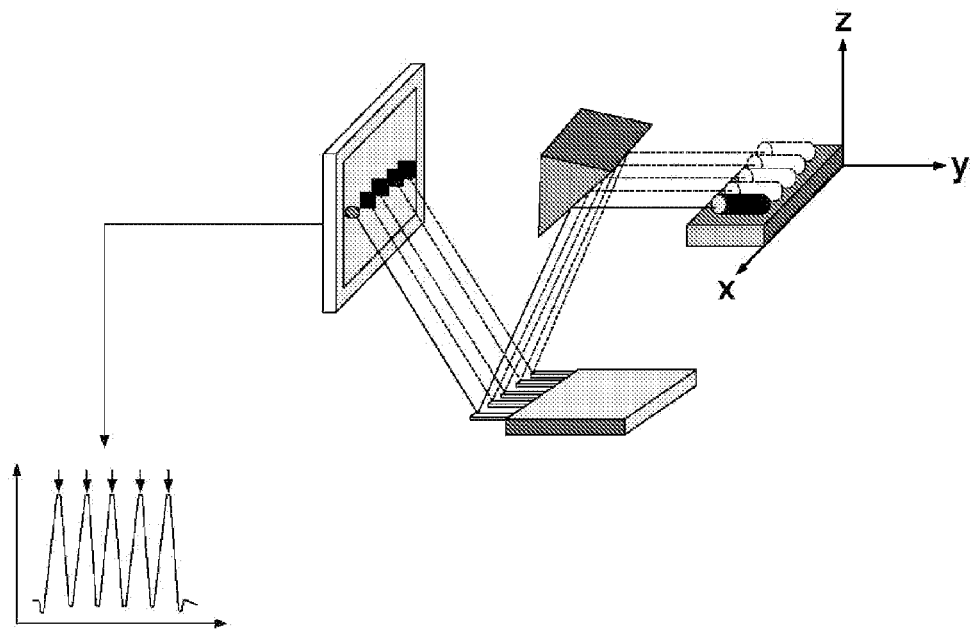
Figure 3A:
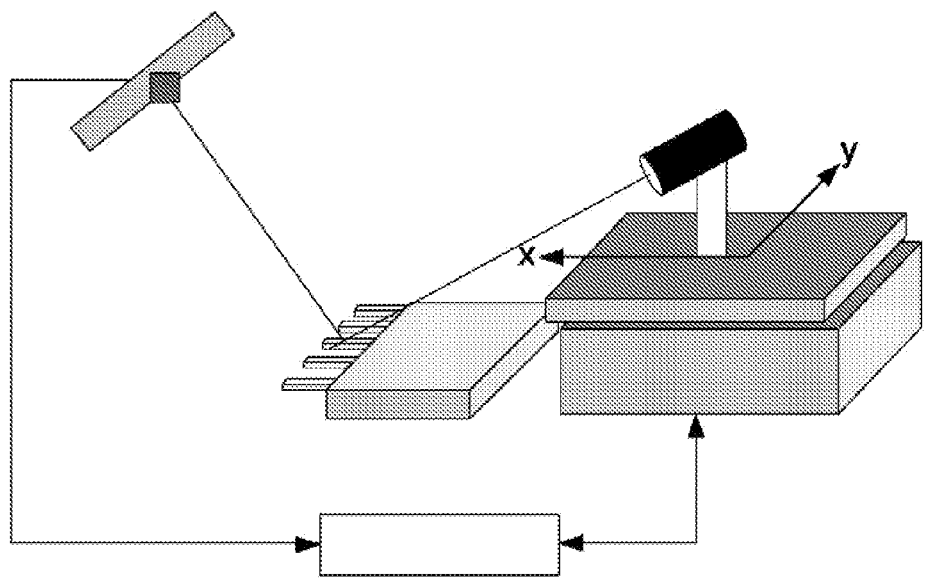
Figure 3B:
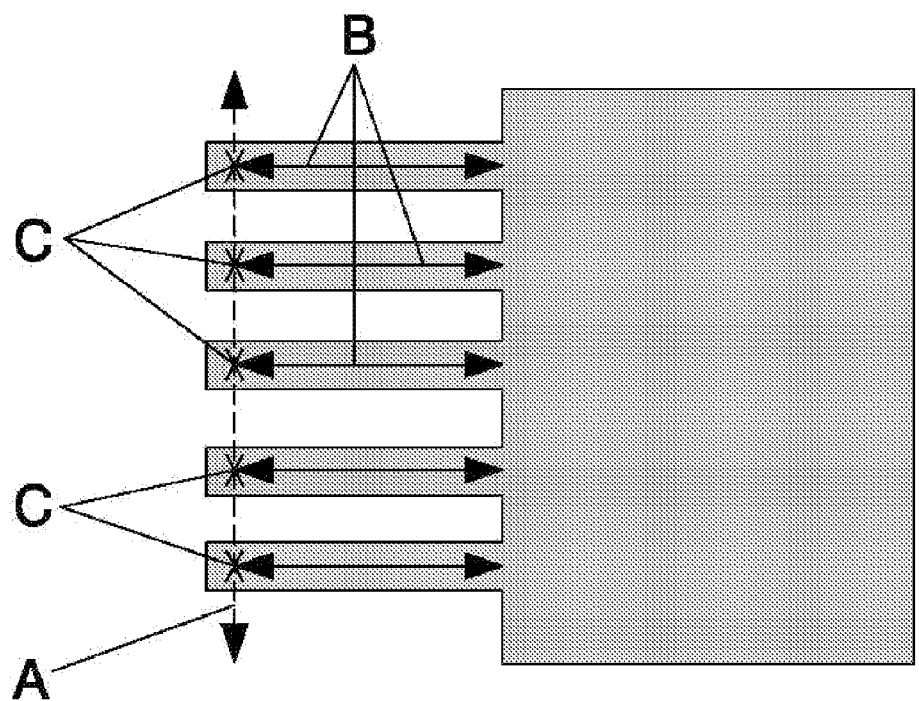
Figure 4:
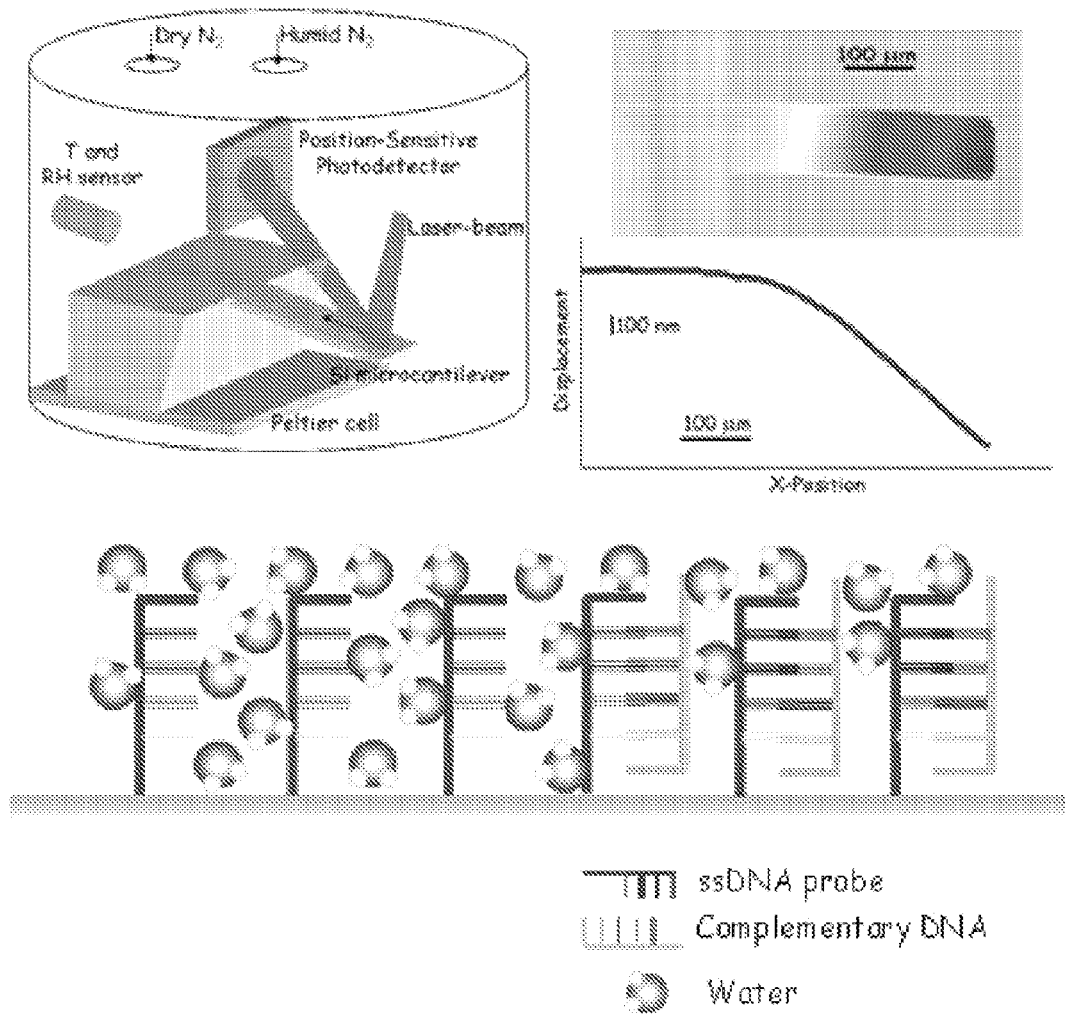
FIG. 4 shows the experimental set-up of the preferred embodiment of the invention.
Figure 8A:
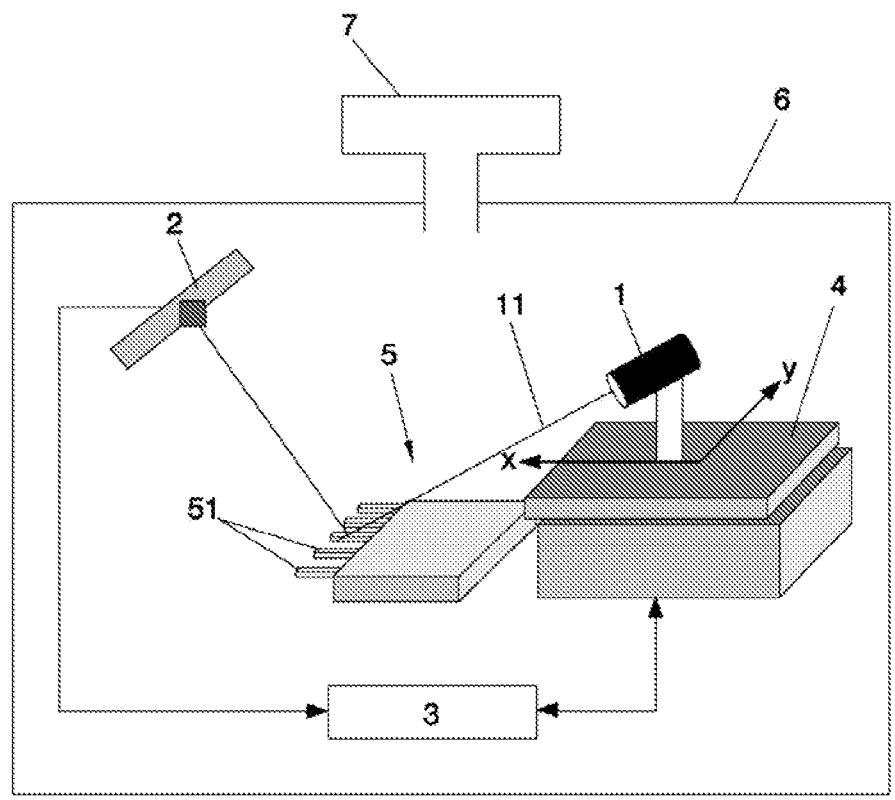
FIG. 8 represents a system for surface inspection according to the invention. A represents the whole system appliance and B the mechanical element
Figure 8B:
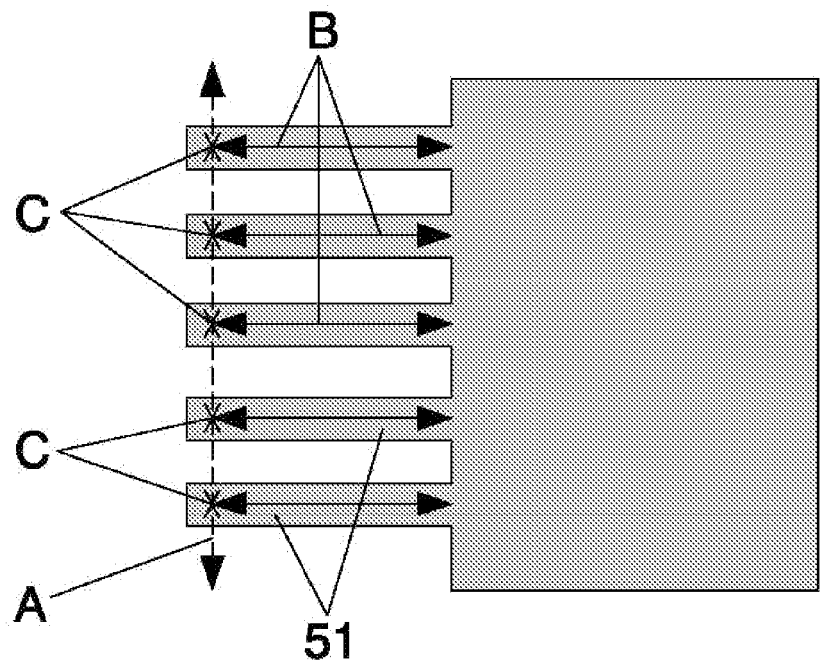

The experimental set-up is illustrated in FIG. 4 and FIG. 8. It was chosen, as an alternative way to enhance the sensitivity of nanomechanical DNA sensors, to externally modulate the interactions between the neighbouring DNA molecules anchored to the cantilever while monitoring how the surface stress changes. Single stranded DNA probes were immobilized on a gold-coated side of microcantilevers via a thiol linker. In a particular realization of the invention, a 16 nt-long ssDNA probe was used with sequence 5'-HS-CT ACCTTTTTTTTCTG-3' (SEQ ID NO: 1). After a long immobilization time (12-24 hours) ssDNA formed a highly packed layer with a surface density of the order of $10^{13}$ cm$^{-2}$, as determined by X-ray photoelectron spectroscopy (XPS) experiments. These densities correspond with inter-DNA distances below 0.3 nm. In this separation range, the intermolecular forces are dominated by the repulsive hydration forces that result from the perturbation of the hydrogen bonding network surrounding the DNA molecules. Hydration forces increase exponentially with a 0.25-0.35 nm characteristic distance. The primary hydration shell is formed by 30 water molecules per nucleotide pair, and that water layer is in an intermediate state between liquid water and ice [M Rovere & P. Gallo, "*Effects of confinement on static and dynamical properties of water*", Eur. Phys. J. E. 12, 77-81 (2003) and N. Floquet, J. P. Coulomb, N. Dufau, G. Andre, & R. Kahn, "*Structural and dynamic properties of confined water in nanometric porous materials*", Physica B 350, 265-269 (2004)]. This first hydration shell plays a key role in the biochemical function and the intermolecular interactions. Based on this previous knowledge, a novel approach was developed to deepen into the physicochemical characterization of the hydration of surface-bound DNA and, in parallel, to enhance the sensitivity of microcantilever-based biosensors. It was demonstrated that it is possible to externally modulate the hydration forces by first placing the DNA-coated microcantilevers in a dry nitrogen atmosphere, and afterwards controlling the degree of hydration by tuning the relative humidity of the incoming nitrogen. This method, applied in a system for surface inspection according to the present invention, allows observing the change of surface stress induced by hydration with an unprecedented sensitivity of one water molecule per nucleotide.

The sequence of experiments in the assays is:
  i) measure the surface stress induced by the hydration/dehydration of cantilevers functionalized with ssDNA by changing RH (relative humidity) from 0 to 100% and reversely;
  ii) expose the functionalized cantilever to a solution of the nucleic acid sample that can contain: a) the fully complementary target ssDNA molecule; b) a ssDNA target with (one to three) mismatches; c) a non complementary ssDNA (negative control); then rinse and dry the cantilever and
  iii) measure the surface stress as the system undergoes a second hydration/dehydration cycle In a particular embodiment of the invention, the fully complementary ssDNA molecule shows the sequence 5'-CAGAAAAAAAGGTAG-3' (SEQ ID NO: 2), whereas the mismatching sequences are: 1) target "T" with a single T/T mismatch near the central position of the duplex (sequence 5'-CAGAAAATAAAGGTAG-3' (SEQ ID NO: 3)); 2) target "TTT" with three subsequent T/T mismatches at the central position (sequence 5'-CAGAAATTTAAGGTAG3' (SEQ ID NO: 4)); 3) target "T . . . T . . . C" with three single mismatches T/T, T/T and C/C separated by three base pairs (sequence 5'-CAGTAAATAAACGTAG-3' (SEQ ID NO: 5)). The theoretical hybridization temperatures for these sequences are 34±1° C., 15±1° C. and 11±4° C., respectively, while it is 43±1° C. for the fully complementary target sequence. The non-complementary ssDNA (negative control) had the sequence 5'-AGCTTCCGTACTCGAT-3' (SEQ ID NO: 6).

II—Immobilization and Hybridization

Figure 5:
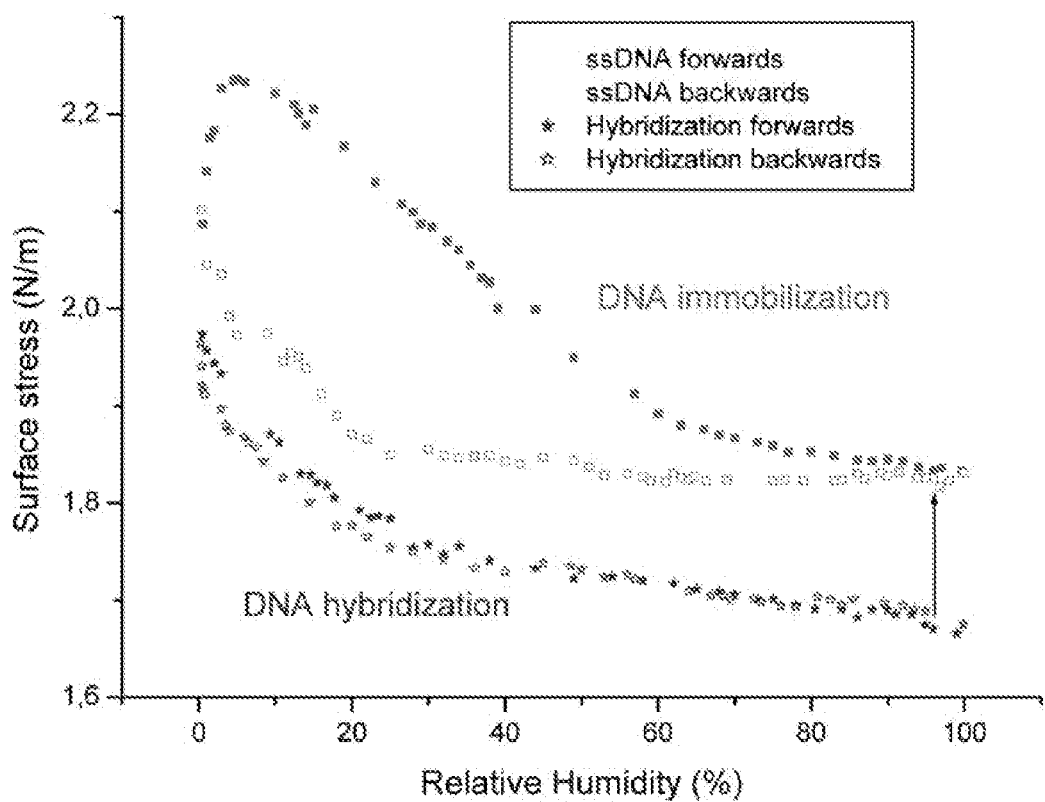
FIG. 5 shows the large hysteresis of a ssDNA sensitized cantilever while subjected to a hydration-dehydration cycle, compared to the greatly reduced hysteresis of the cantilever with dsDNA (after full complementary probe-target hybridization) subjected to the same hydration-dehydration cycle.

The response of the ssDNA sensitised cantilever to a hydration-dehydration cycle shows large hysteresis, whereas for the cantilevers that have undergone a fully complementary hybridization the hysteresis is greatly reduced (see FIG. 5). Fully hybridized DNA layers are known to present impermeabilization properties due to the steric constraints given by the densely packed molecules in the layer, while the ssDNA layer is prone to the intercalation of water molecules inside the biopolymer that would explain the large tensile stress observed when the layer is hydrated [J. Mao, S. Chang, S. Yang, Q. Ouyang & L. Jian, "Tunable non-equilibrium gating of flexible DNA nanochannels in response to transport flux", Nature Nanotechnology 2, 366-371 (2007) and B. Schneider & H. M. Berman, "Hydration of the DNA bases is local", Biophys. J. 69, 2661-2669 (1995)]. For the sensitised cantilever (ssDNA), the surface stress undergoes a sharp rise (tensile) during the initial hydration up to a relative humidity of 5%. The surface stress then decreases until it is relatively hydration independent for RH>60%.

Figure 6:
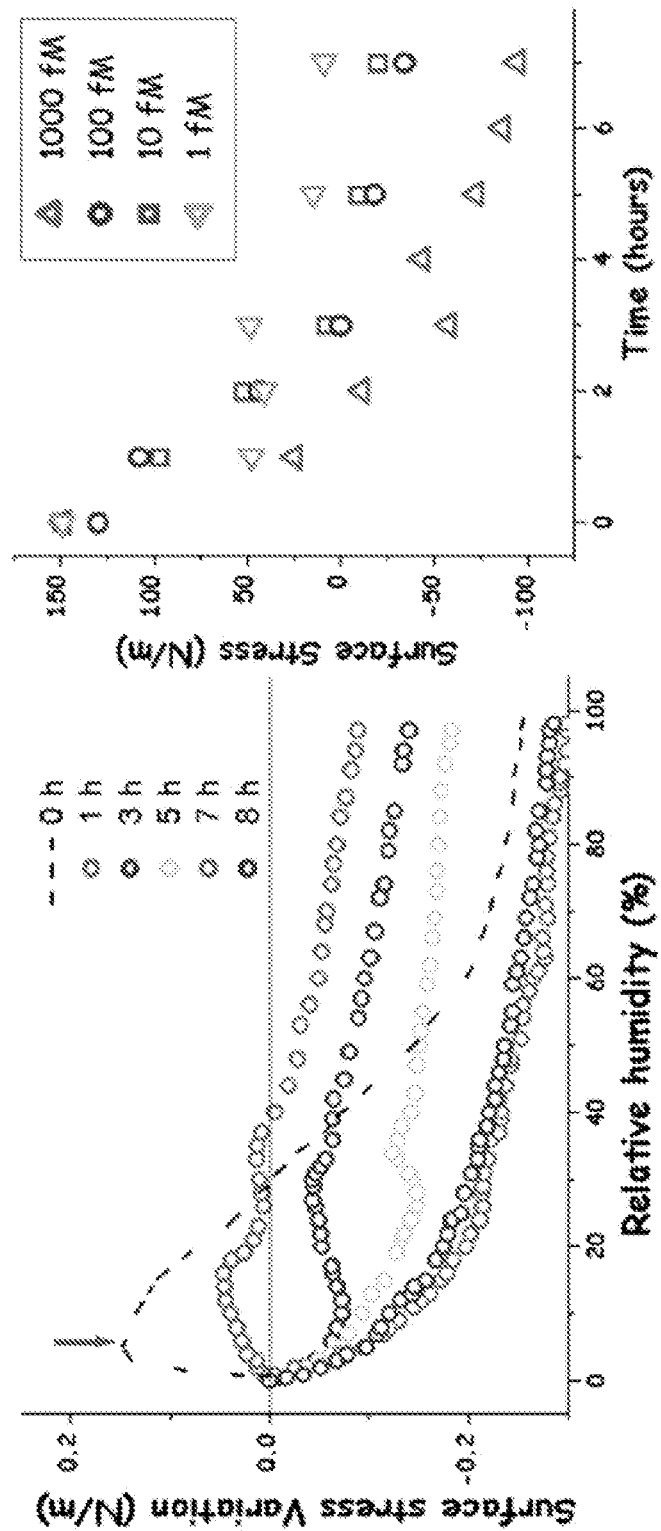
FIG. 6. LEFT: Surface stress change during hydration cycle for dsDNA at different times and a target concentration of 1 pM. RIGHT: Surface stress variation with time at RH=5% for different concentrations (from 1 fM to 1000 fM) of the fully complementary DNA target.

It is interesting to monitor the response with time of the ssDNA layer when immersed in a very diluted solution of complementary ssDNA. FIG. 6A shows the surface stress vs the RH for the silicon cantilever sensitised with the probe ssDNA (dashed line) and for the same sensitised cantilever after exposure to the complementary target DNA at 1 pM concentration and different exposure times (from 0 h to 8 h) in PBS buffer (137 mM NaCl, 2.7 mM KCl, 8 mM $Na_2HPO_4$, 2 mM $KH_2PO_4$; pH=7.5) at a hybridization temperature of 21° C. The hybridized cantilever achieves an asymptotic response for probe-target exposures longer than 6 hours. The surface stress monotonically decreases (compressive) up to about 0.2 N/m from the dehydrated to the hydrated state, being most of the decrease produced between RH=0% and 25%. The response of the attached ssDNA probe to the complementary ssDNA for shorter exposure times shows an intermediate behaviour, in which two peaks are observed at RH of 10-20% and 30-40% respectively. These peaks could correspond to structural transitions in the DNA double helix (A to B forms).

Fully hybridized complementary DNA (dsDNA) layer shows a very different behaviour during hydration-dehydration cycle. The hysteresis is greatly reduced, because of the absence of compressive stress in the hydration cycle at low RH. This fundamental difference arises from the DNA interactions with intercalated water molecules forming a stabilizing structure with the DNA backbone and the nucleobases. Moreover, the compressive response of dsDNA at low RH (0-5% range), contrarily to the tensile stress in a non-hybridized ssDNA layer, can be qualitatively related to the hybridization of the ssDNA probe with the target molecule. This effect talks about the high performance of the system for biosensing applications.

III—Sensitivity and Specificity of the System

Figure 7:
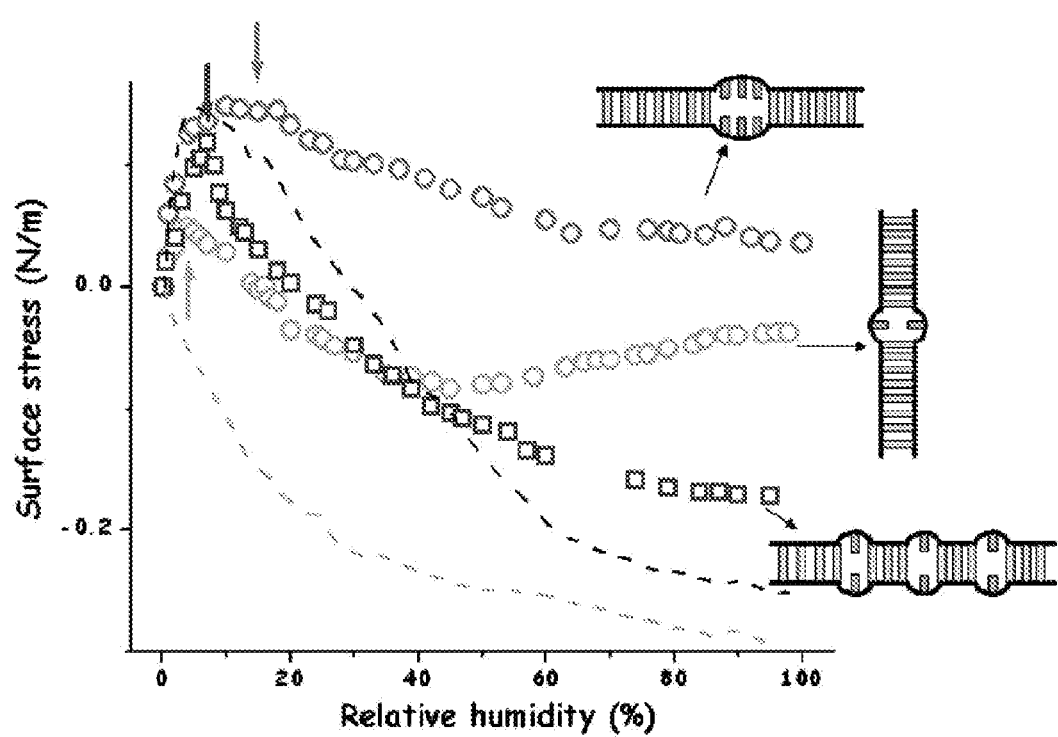
FIG. 7 shows surface stress variation at the surface of the cantilever during hydration for three different mismatched DNA target sequences.

Among the different parameters that can be measured in a hydration-dehydration cycle, we have found the surface stress during the initial hydration to be very sensitive to the DNA form, i.e., non hybridized ssDNA or hybridized dsDNA. Therefore, we have chosen this to be the measurement parameter of the biosensor. We plot in FIG. 6B the surface stress variation at RH=5% with respect to the response of a fully non-complementary ssDNA negative control, that is identical to the response of the sensitized cantilever, as a function of the hybridization time for different target concentrations. In all curves, the surface stress rapidly decreases during the first three hours of exposure to the complementary sequence. More importantly, it was found that the technique is able to detect a concentration of target DNA of 1 fM for exposure times of one hour, the signal detected being of 100 mN/m. This is well above the 1 mN/m detection noise of the system. We relate this unprecedented sensitivity to the physical steric crowding. In highly packed ssDNA monolayers, the formation of a relative small number of duplexes can have an important impact in the collective properties of the DNA film due to the exponential and cooperative nature of the hydration forces. Finally, in order to characterize the specificity of the developed biosensor, we exposed the sensitised cantilevers to three mismatched target sequences at a higher concentration of 1 µM (FIG. 7). As mentioned above, three mismatched target ssDNAs were designed: target "T" with a single T/T central mismatch, target "TTT" with three subsequent T/T mismatches at the central position, and target "T . . . T . . . C" with three single mismatches T/T, T/T and C/C separated by three A/T base pairs.

In these experiments, whereas for the fully complementary DNA the surface stress decreases with the relative humidity, all the mismatched DNAs give an initial increase of the surface stress (tensile). Interestingly, this tensile surface stress peak appears for all the studied mismatched sequences, but the peak position occurs at different RHs. Since the hybridization was performed in all experiments at 21° C., significant variations are not expected in the hybridization yield of the fully complementary and single-mismatched sequences (theoretical calculations show that the discriminatory temperature for those targets should be expected to lie in the range 34-43° C.). We propose that this initial hydration-induced tensile stress is due to the stabilization of a mismatch-induced "bubble" in the duplex by hydrogen bonding. As a consequence, a relevant feature of the method developed is that, contrarily to what happens in DNA microarrays and other current biosensors, the differential behaviour of the mismatched target does not rely on its tendency to de-hybridize at an optimized, fine-tuned working temperature, but on the particular interaction of the mismatch induced "bubble" with water molecules at any temperature far below its melting temperature.

In conclusion, the intermolecular forces in monolayers of nucleic acids critically depend on the degree of hydration.

The small permeability of the ssDNA monolayers makes that hybridization of about one target molecule per million of probes produces a dramatic effect in the pattern of the tension with respect to the hydration. This principle also allows the discrimination of single mutations and even the discern between different mismatched sequences. The unprecedented sensitivity achieved by hydration of DNA layers has not been reached by any biosensor able to detect unlabelled target samples. We anticipate our experiments to be a starting point for rapid and straightforward genotyping or SNP mapping at room temperature, without need of sample amplification and labelling. Moreover, these novel phenomena can be exploited for unique potential applications in nanofluidics, drug delivery and sensing.

The invention claimed is:

1. A method for detection of a selected type of nucleic acid molecules in a sample, comprising:
    a) bringing a receptor surface of a micromechanical element in contact with the sample, said receptor surface being arranged to interact with said nucleic acid molecules when said nucleic acid molecules are present in said sample, the micromechanical element being arranged so that at least one detectable mechanical feature of said micromechanical element changes when said receptor surface interacts with said nucleic acid molecules and changes with a variation in a humidity or a relative humidity, wherein respectively different nucleic acid molecules have different responses to changes in the humidity or the relative humidity;
    b) measuring said mechanical feature while being subjected to the variation in the humidity or the relative humidity, to obtain data regarding said mechanical feature for a plurality of respective different values of the humidity or the relative humidity while said receptor surface interacts with said nucleic acid molecules, said mechanical feature being selected from the group consisting of a curvature of a portion of the micromechanical element, a position of a portion of the micromechanical element, at least one vibration characteristic of the micromechanical element, and a surface stress on a portion of the mechanical element; and
    c) based on said data and said different values of said condition, determining if the sample contains said selected type of nucleic acid molecules or associative phenomena between the receptor surface and said selected type of nucleic acid molecules.

2. The method according to claim 1, wherein the micromechanical element is a microcantilever, one surface of said microcantilever being the receptor surface.

3. The method according to claim 2, wherein said microcantilever is part of a microcantilever array, wherein the method is performed on said microcantilever array so as to detect the presence of a plurality of different types of nucleic acid molecules in the sample, said different types of nucleic acid molecules being associated with different microcantilevers of said microcantilever array.

4. The method according to claim 1, wherein said determining determines the associative phenomenon between the receptor surface and the nucleic acid molecules, and the associative phenomenon determined is selected from the group consisting of a DNA-DNA hybridization phenomenon, a DNA-PNA hybridization, a DNA-RNA hybridization, a PNA-RNA hybridization, and a ribozyme-substrate interaction.

5. The method according to claim 1, wherein said determining determines the associative phenomenon representing a DNA hybridization phenomenon characterized by containing one or more nucleotide mismatches between a DNA probe and a DNA target molecule.

6. The method according to claim 1, wherein said measuring said mechanical feature comprises directing a light beam against a surface of said micromechanical element, receiving a portion of the light beam reflected off said micromechanical element with a position sensitive detector arranged to produce at least one output signal in response to receipt of at least said reflected portion of the light beam.

7. The method according to claim 1, wherein in addition to the variation in the humidity or relative humidity, a pH of a fluid in which the micromechanical element is placed is varied during said measuring.

8. The method according to claim 1, wherein in addition to the variation in the humidity or relative humidity, an ionic strength of a fluid in which the micromechanical element is placed is varied during said measuring.

9. The method according to claim 1, wherein in addition to the variation in the humidity or relative humidity, a relative content of a mixture of gases in which the micromechanical element is placed is varied during said measuring.

10. The method according to claim 1, wherein in addition to the variation in the humidity or relative humidity, a relative content of a mixture of liquids in which the micromechanical element is placed is varied during said measuring.

11. The method according to claim 1, wherein in addition to the variation in the humidity or relative humidity, a radiation to which the receptor surface of the micromechanical element is subjected is varied during said measuring.

12. The method according to claim 1, wherein in addition to the variation in the humidity or relative humidity, an electric field to which the receptor surface of the micromechanical element is subjected is varied during said measuring.

13. The method according to claim 1, wherein in addition to the variation in the humidity or relative humidity, a magnetic field to which the receptor surface of the micromechanical element is subjected is varied during said measuring.

14. The method according to claim 1, wherein said determining determines the associative phenomenon representing a DNA-DNA hybridization phenomenon.

15. The method according to claim 1, wherein said determining determines the associative phenomenon representing a DNA-PNA hybridization phenomenon.

16. The method according to claim 1, wherein said determining determines the associative phenomenon representing a PNA-RNA hybridization phenomenon.

17. The method according to claim 1, wherein said determining determines the associative phenomenon representing a ribozyme-substrate interaction phenomenon.

18. A method for sensing nucleic acid molecules in a sample, comprising:
    a) providing at least one micromechanical element having a receptor surface, having at least one mechanical property selected from the group consisting of a curvature of a portion of the micromechanical element, a position of a portion of the micromechanical element, at least one vibration characteristic of the micromechanical element, and a surface stress on a portion of the mechanical element, which is responsive to both nucleic acid molecules in the sample and a variation in a humidity or a relative humidity in an environment surrounding the receptor surface, wherein different nucleic acid molecules on the receptor surface cause the at least one mechanical property to respond differently to changes in the humidity or the relative humidity;

b) interacting the receptor surface of the micromechanical element with nucleic acid molecules present in the sample;
c) measuring the mechanical property over a plurality of different values of the humidity or the relative humidity surrounding the receptor surface, while the receptor surface interacts with the nucleic acid molecules in the sample, to obtain a plurality of data values representing the at least one mechanical property obtained for the plurality of different values of the humidity or the relative humidity; and
d) determining at least one of a presence of a selected type of the nucleic acid molecules and an associative phenomena of the selected type of nucleic acid molecules in the sample, based on the plurality of data values.

* * * * *

```
                       SEQUENCE LISTING

<160> NUMBER OF SEQ ID NOS: 6

<210> SEQ ID NO 1
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 1 ctacctttt tttctg                                                   16

<210> SEQ ID NO 2
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 2
cagaaaaaaa aggtag                                                  16

<210> SEQ ID NO 3
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 3
cagaaaataa aggtag                                                  16

<210> SEQ ID NO 4
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 4
cagaaattta aggtag                                                  16

<210> SEQ ID NO 5
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 5
cagtaaataa acgtag                                                  16

<210> SEQ ID NO 6
<211> LENGTH: 16
<212> TYPE: DNA
<213> ORGANISM: Artificial sequence
<220> FEATURE:
<223> OTHER INFORMATION: synthetic oligonucleotide
```

```
<400> SEQUENCE: 6
agcttccgta ctcgat                                                    16
```